United States Patent [19]

Borsanyi

[11] Patent Number: 4,671,792
[45] Date of Patent: Jun. 9, 1987

[54] PRESSURE-REGULATING PERISTALTIC PUMP

[75] Inventor: Alexander S. Borsanyi, Newport Beach, Calif.

[73] Assignee: American Hospital Supply Corporation, Evanston, Ill.

[21] Appl. No.: 830,694

[22] Filed: Feb. 18, 1986

[51] Int. Cl.⁴ ............................................. A61M 5/00
[52] U.S. Cl. ............................. 604/153; 128/DIG. 12; 417/474
[58] Field of Search ............................ 604/151–153; 128/DIG. 12; 417/474, 475

[56] References Cited

U.S. PATENT DOCUMENTS

| | | | |
|---|---|---|---|
| 2,877,714 | 3/1959 | Sorg et al. | 417/474 X |
| 3,990,444 | 11/1976 | Vial | 604/153 |
| 4,373,525 | 2/1983 | Kobayashi | 417/474 X |
| 4,482,347 | 11/1984 | Borsanyi | 604/153 |
| 4,561,830 | 12/1985 | Bradley | 417/474 |

Primary Examiner—Dalton L. Truluck
Attorney, Agent, or Firm—Tilton, Fallon, Lungmus

[57] ABSTRACT

Controlling maximum fluid pressure at the outlet end of a peristaltic pump of the general type disclosed in U.S. Pat. No. 4,482,347 is achieved by supporting the resilient tubing of the pump in the trough of a rigid but movable platen mounted upon a compression pad or spring arrangement that resists platen movement until a back pressure of predetermined magnitude occurs, at which time the plate is displaced to reduce pumping efficiency and prevent further increases in outlet pressure.

22 Claims, 7 Drawing Figures

PRESSURE-REGULATING PERISTALTIC PUMP

BACKGROUND

U.S. Pat. No. 4,482,347 discloses a peristaltic pump which, because of its compactness and simplicity of construction, and its precise, accurate, and reliable operation, is particularly suitable for medical use in a fluid infusion or administration system or in a system for withdrawing fluids, such as wound, urine, pleura, or other drainage systems. The pump includes a series of bearing assemblies each having concentric inner and outer members capable of free rotation with respect to each other. The inner members are concentrically mounted upon a power-driven shaft with the centers of the inner members equidistant from the axis of the shaft and spaced at uniform angular distances thereabout to describe a helix about the axis of the drive shaft. A resilient tube extends along a line parallel with the shaft and is supported by a platen so that the tube is sequentially compressed by each of the outer bearing members of the series, thereby driving fluid through the resilient tube. A thin elastomeric membrane is interposed between the outer bearing members and the tube with the membrane in continuous contact with the tube during pump operation.

Such a pump is of positive action in its operation and is capable of generating substantial outlet pressures. While maximum discharge pressure may be controlled by simply discontinuing pump operation, situations exist in arthroscopic surgery and other medical and non-medical operations where interrupting pump operation, and the resultant decreases in pressure which then occur, are undesirable. What is instead needed is some means that operates independent of flow rate for insuring that a selected maximum discharge pressure is not exceeded. A further objective would be to attain such control over maximum outlet pressure while at the same time providing a unit which is simple and reliable in operation, is relatively compact, and utilizes relatively inexpensive tubing that may be economically discarded after a single interval of use.

Other types of peristaltic pumps are disclosed in the references cited in the aforementioned patent and are further represented by U.S. Pat. Nos. 4,373,525, 3,990,444, 3,542,491, and 4,029,441. U.S. Pat. No. 4,373,525 discloses a peristaltic pump with slidable fingers that engage a tube supported by a spring-loaded pressure plate, with the addition of a pivotal arm having "pressing parts" at its opposite ends for detecting pressure changes and triggering a suitable alarm; U.S. Pat. No. 3,990,444 ws a pump having a tube similarly supported by a spring-loaded pressure plate and with multiple rollers carried by a wheel that rotates in the same plane as the tubing; U.S. Pat. No. 3,542,491 discloses a pump also having rollers that are moved along a section of resilient tubing to drive fluid through that tubing; U.S. Pat. No. 4,029,441 discloses tubing formed by a folding operation which is held in place by jaws and saddle elements to insure a desired pumping action by pump rollers as they are advanced along the tube.

SUMMARY OF THE INVENTION

One aspect of this invention lies in the discovery that pressure regulation of a peristaltic pump of the type disclosed in the aforementioned and co-owned U.S. Pat. No. 4,482,347 may be achieved simply and effectively, and independently of rate of flow, by supporting the straight section of tubing by means of a platen which automatically moves away from the axis of the bearing assemblies when back pressure exceeds a predetermined maximum level, thereby reducing pumping efficiency to just the extent necessary for maintaining, but not exceeding, such maximum pressure. Specifically, the platen assembly takes the form of a support frame which is fixed in relation to the pump axis when the pump is in operation, a rigid platen plate having an elongated channel or trough that supports the straight section of resilient tubing to be compressed by the bearing assemblies and compression means interposed between the frame and the floating rigid plate for holding the tubing section in position for sequential compression by the bearing assemblies. The compression means may take the form of an elastomeric foam pad or a series of compression springs disposed between the frame and floating plate. In either case, the compression means is only slightly or partially compressed during normal pump operation but is more fully compressed to permit substantial displacement of the plate when a predetermined maximum back pressure is exceeded.

The trough or channel of the floating plate has a radius of curvature, when viewed in cross section, that is only slightly greater than the outside radius of the outer bearing members of the pump. Such a relationship permits the use of resilient tubing that has a relatively large diameter in relation to the size of the bearing assemblies, without risk that unintended backflow might occur through the tubing during normal pumping operation. The result is a pump of relatively high capacity for its size and operating speed. Ideally, an elastomeric membrane is disposed between the bearing assemblies of the pump and the resilient tubing, and, if desired, a resilient liner may be provided along the trough or channel of the rigid plate of the platen assembly.

Other features, advantages, and objects of the invention will become apparent from the specification and drawings.

DRAWINGS

DETAILED DESCRIPTION OF PREFERRED EMBODIMENTS

Figure 1:
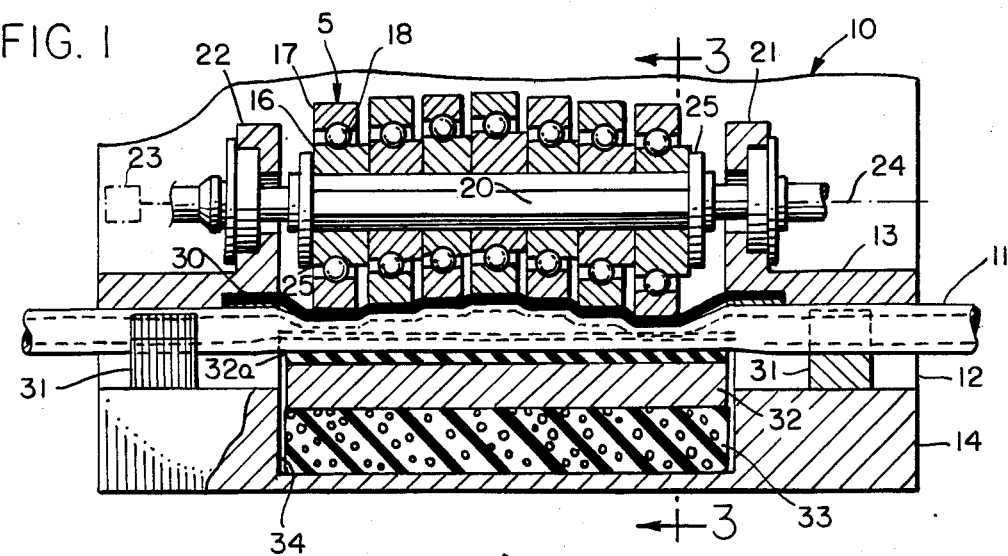
FIG. 1 is a longitudinal sectional view of a pumping apparatus embodying this invention.

Referring to the drawings, the numeral 10 generally designates a peristaltic pump for metering fluid through resilient tubing 11. The tubing may be formed of an elastomeric material such as, for example, silicone rubber; however, it is not necessary, at least in all cases, that the tubing material be elastomeric but only that it be sufficiently resilient to permit full collapse and recovery upon the application and removal of compressive forces. Resilient polyvinyl chloride tubing has been found effective, and it is believed that any of a wide variety of resilient similar polymeric but non-elastomeric materials might be used.

Except for the differences described herein, the peristaltic pump 10 is essentially the same as the pump shown and described in Borsanyi U.S. Pat. No. 4,482,347, the disclosure of which is incorporated by reference herein. The pump includes a housing 12 composed of a pair of sections 13 and 14 which are locked together in the relationship shown in FIG. 1 when the pump is operated but which are hingedly or otherwise separably connected to permit insertion and removal of tubing 11. In the illustration given, sections 13 and 14 are depicted as upper and lower sections, respectively, and while reference may be made to such orientation for clarity of description it is to be understood that the orientation is not critical and that the pump may be operated effectively in any suitable position.

The pump mechanism includes a series of bearing assemblies 15 each having inner and outer bearing members 16 and 17, respectively. Preferably, the inner bearing member 16 takes the form of an inner bearing race, the outer member 17 constitutes an outer race, and anti-friction bearing elements 18 are disposed therebetween. Such anti-friction bearing elements would normally consist of ball bearings, but the use of various types of roller bearings is possible. Furthermore, other types of bearing assemblies, such as self-lubricating sleeve bearings, might be advantageously used.

Each inner race or member 16 is mounted eccentrically upon a drive shaft 20, and the shaft is in turn journaled in brackets or mounting elements 21 and 22. One end of the shaft is operatively connected to power means in the form of stepping motor 23.

Each inner race or member 16 is eccentrically mounted upon shaft 20 with the centers of all such races being equidistant from the axis 24 of the drive shaft and with the angular spacing between all of such centers being essentially the same and the sum of the angular spacing being 360°. Where a series of seven bearing assemblies is provided as shown, the incremental angular distance between the centers of the inner races should be 360° divided by 7, or approximately 51.43°. A greater or smaller number of bearing assemblies may be provided, although the preferred range is believed to be 3 to 30 such assemblies. Of particular importance is the fact that the series of bearing assemblies must be mounted upon the drive shaft 20 so that the centers of the inner races describe a spiral or helix of at least 360° about the drive shaft axis.

The inner races 16 may be secured upon the shaft 20 in any suitable manner. In the embodiment illustrated, shaft 20 has a central portion of non-circular (heptagonal) cross sectional outline and the eccentrically-disposed openings 16a in the respective inner races 16 are of the same configuration so that the eccentric bearings may be incrementally positioned upon the shaft with their centers helically oriented. The inner races are thereby secured against independent relative rotation with respect to shaft 20, and locking elements 25 are secured to the shaft at opposite ends of the series of bearing assemblies 15 to hold the series against axial displacement.

A portion of the resilient polymeric tube 11 is supported with its longitudinal axis parallel with the rotational axis 24 of shaft 20 and with a linear zone of one surface of an elastomeric membrane 30 in contact with the tube. Tube retaining means in the form of a pair of mounting brackets or clamps 31 are provided by one of the housing sections (the lower section 14 in FIGS. 1 and 2) for frictionally retaining the tubing in place and for insuring that the portion of the tube disposed between the brackets is straight and is in parallel alignment with the rotational axis of the drive shaft.

Figure 2:
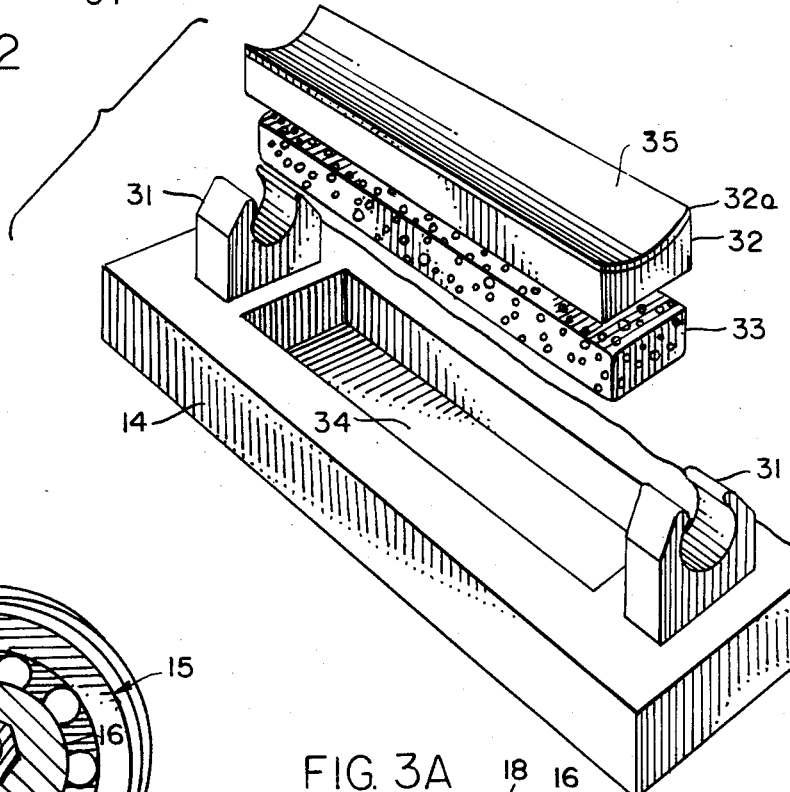
FIG. 2 is an exploded perspective view of the platen assembly for such apparatus.
Figure 3:
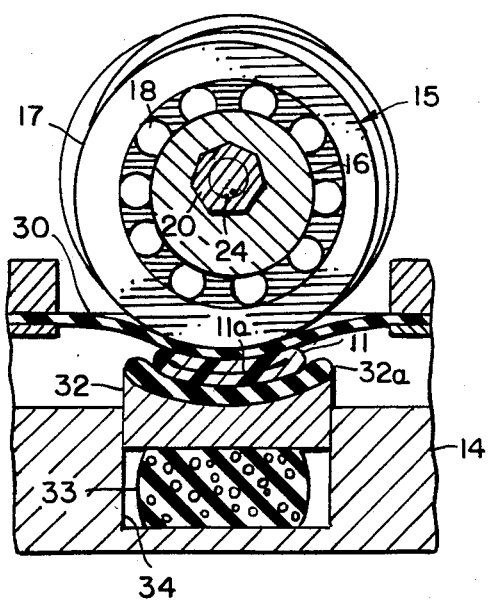
FIG. 3 is an enlarged sectional view taken along line 3—3 of FIG. 1.

The imperforate elastomeric membrane 30 is interposed between tube 11 and the cylindrical surfaces of the outer bearing members or races 17 as illustrated in FIGS. 1 and 3. The membrane is planar in an untensioned state and assumes the configuration shown in these figures because of the distortions developed by bearing assemblies 15. Ideally, the membrane is secured to the upper housing section 13 and separates or isolates the pump mechanism from tubing 11. Any suitable means may be used to secure the periphery of the membrane to casing or housing section 13.

A platen assembly supports the tube in contact with the underside of membrane 30 and in proper position for compression by bearing assemblies 15. The platen assembly includes housing section 14, a rigid platen element or plate 32, and compression means 33 which, in FIGS. 1 and 3, takes the form of an elastomeric foam pad or cushion. The plate 32 is rectangular in outline and elongated in the direction of tubing 11. Similarly, the compression pad or cushion 33 has a rectangular outline similar to that of rigid plate 32 although, as shown in FIGS. 1 and 3, the pad may be shorter and narrower than plate 32. Both the compression pad and the lower portion of the rigid plate are received within a rectangular recess 34 formed in housing section 14. The housing section therefore defines a frame for retaining plate 32 and compression pad 33 and for maintaining the plate in proper supporting relation with respect to tubing 11. The plate 32 and its facing 32a are depicted as being slightly shorter than recess 34 to allow the plate to float more freely, even rock slightly, upon pad 33 in that recess. As shown most clearly in FIG. 2, the mounting brackets 31 are located at opposite ends of the elongated rectangular recess 34.

Each bearing assembly 15 has its inner race 16 eccentrically mounted so that its center moves between one extreme position in which it is spaced maximally from the platen and the lumen 11a of the tube is substantially fully open (FIG. 6) and the other extreme position in which the center of the inner race is spaced minimally from the platen and the lumen of the tube is closed (FIG. 3). To reduce torque peaks that develop as each bearing assembly sweeps through the lumen-occluding position of FIG. 3, especially when two such assemblies (the first and last of the series) simultaneously compress and substantially close the tube, the plate 32 may be provided with a resilient facing 32a engaging and supporting tube 11. The facing must not be so compliant that it will allow outward displacement of the tube in preference to complete occlusion of that tube. The tube should close as shown in FIG. 3 with the resilience of facing 32a serving the primary purpose of reducing the torque peak once such occlusion has taken place. It is to be understood that facing 32a, although highly advantageous, is optional, and that its presence does not alter the fact that plate 32 of the platen assembly is rigid and provides firm support for tubing 11.

The upper surface of plate 32 (and the upper surface of facing 32a, if provided), is arcuate when viewed in transverse section. Specifically, the upper surface 35 defines an elongated channel or trough for receiving and supporting tubing 11. The radius of transverse curvature of the trough is slightly greater than the radius of curvature of the outer surface of each outer bearing race or member 17. Ideally, the radius of curvature of the trough should equal the sum of the radius of each bearing assembly, plus the extent of its eccentricity, plus double the wall thickness of tube 11, plus the thickness of membrane 13 (where the membrane is included). Since the membrane is relatively thin (its thickness is exaggerated in the drawings for clarity of illustration), it may be stated that the radius of curvature of the trough approximates the radius of each bearing assembly, plus its eccentricity, plus 2 times the wall thickness of the tube. The result is that when tube 11 is fully compressed and its lumen is occluded by a bearing assembly as depicted in FIG. 3, the curvatures of the bearing assembly, the collapsed wall portions of the tubing 11, and the trough or upper surface of the floating plate (whether faced or not) are all concentric.

Such a curvature of the trough has a number of important advantages. It insures that when the tubing is compressed, as shown in FIG. 3, its lumen 11a is fully closed or occluded. The lumen appears as a tightly closed slit without any lateral bypass channels that might otherwise be present at opposite ends of that slit if the platen were flat rather than transversely curved. Furthermore, the curvature of the trough permits usage of relatively large diameter resilient tubing 11 (in relation to the diameter of bearing assemblies 15) without risk that undesirable leakage might occur when the tube is in its compressed state. Because of the relatively large size of the tubing in relation to the diameter of the bearing assemblies, the pump has high pumping capacity for its size and operating speed. In addition, the curvature of the trough contributes significantly in retaining tube 11 in proper position during a pumping operation, even when the support plate 32 shifts in its position because of pressure fluctuations near the maximum level. The curvature thus reduces the need for elastomeric membrane 30. While the presence of the thin membrane is still highly advantageous to insure against lateral displacement of the tube during pump operation and to isolate the pump mechanism from tubing 11 and the platen assembly, thereby protecting the pump mechanism from contact with fluids, particulates, and, in general, outside contaminants, the membrane may nevertheless be omitted in some cases because of the stabilization of the tube provided by the arcuate trough.

Although the plate 32 is slidably received in recess 34 for upwardly and downward movement therein, such plate is normally held stationary in the operative position illustrated in FIG. 3 by the compression means (pad) 33. As each bearing assembly urges tube 11 into its fully closed position, only slight or partial compression of pad 33 occurs. In other words, the material of pad 33 is selected so that its resistance to compression generally exceeds the resistance of tube 11 against becoming fully collapsed. Therefore, during normal pump operation, or at least until resistance to outflow from the pump exceeds a predetermined maximum level, pad 33 is no more than partially compressed.

Figure 4:
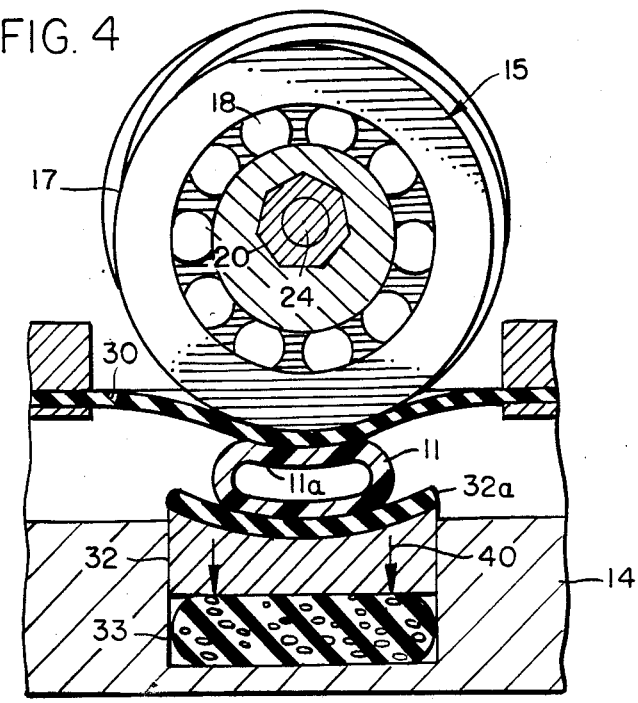
FIG. 4 is a sectional view similar to FIG. 3 but showing displacement of the floating plate for regulating back pressure.

The material and dimensions of the pad are selected so that its resistance to compression will be overcome when a predetermined maximum fluid pressure develops in tube 11 downstream of the pump. For example, for a pump to be used in arthroscopic surgery, it has been found that a maximum discharge pressure of 20 psig is appropriate. Greater pressures might result in rupture of the tubing and possibly produce other complications in the operative procedure. The compression pad is therefore dimensioned and formed of an elastomeric material (foam rubber) that cannot maintain the platen plate 32 in its upwardly extended position (FIG. 3) when fluid pressures within tubing 11 on the downstream side of the pump exceed 20 psig. When such a condition arises, the floating plate 32 is forced downwardly in the direction of arrows 40, compressing pad 33 and allowing the lumen 11a of the resilient tube 11 to open (FIG. 4). Pumping efficiency drops sharply since liquid in the tube may flow in a reverse direction to the extent permitted by retraction of the floating platen plate 32. Such retraction is modulating and self-correcting; that is, the plate 32 retracts only to the extent necessary to keep fluid pressure from substantially exceeding a preselected maximum pressure (20 psig in the example given above), and once the downstream pressure drops below the selected maximum level the floating plate will return to its original position, thereby restoring pumping efficiency (FIG. 3).

Figure 5:
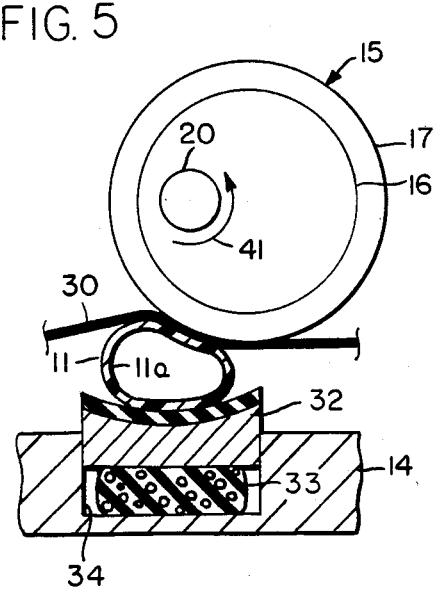
FIG. 5 is a somewhat schematic view illustrating the relationship of one bearing assembly, the resilient tubing, and the platen assembly when the pump shaft has rotated approximately 90° from the position of FIG. 3.
Figure 6:
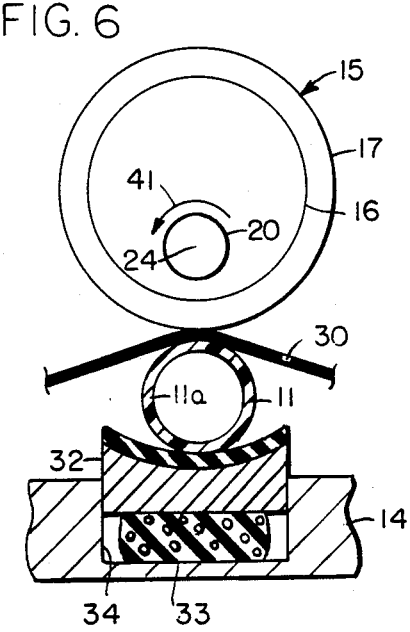
FIG. 6 is a schematic view similar to FIG. 5 but illustrating the relationship of parts when the pump shaft has rotated approximately 180° from the position shown in FIG. 3.

FIGS. 5 and 6 schematically depict a bearing assembly of the pump in different stages of operation. Thus, FIG. 5 shows the bearing assembly 15 when the drive shaft has rotated clockwise, in the direction of arrow 41, 90° from the position shown in FIG. 3. It will be observed that the trough contributes in retaining the tube 11 in its original position despite the fact that bearing assembly 15 is displaced laterally because of the eccentric mounting of its inner race 16 on drive shaft 20. When that shaft has rotated 180° from its original position, the parts assume the relationship depicted in FIG. 6. Continued rotation of the shaft results in compressive action of the bearing assembly 15 until full compression is again achieved (FIG. 3).

Figure 3A:
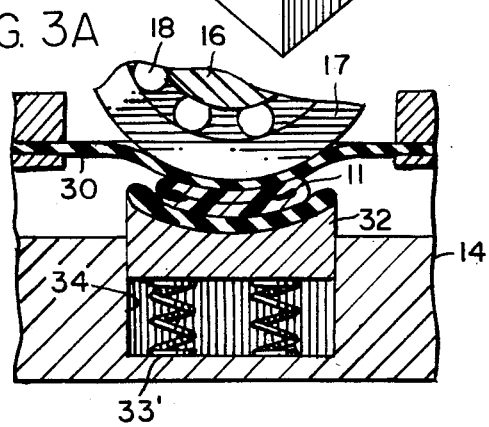
FIG. 3A is a sectional view similar to FIG. 3 but illustrating alternate pressure-limiting compression means.

The compression means 33 has been shown and described as being formed of compressible elastomeric material with low hysteresis such as silicone foam rubber. It is to be understood that similar results may be achieved by utilizing spring means or any other compressible elements that resist compression until the discharge pressure in the line exceeds a preselected maximum level and that restore the floating platen plate to its extended position when the discharge pressure drops below that level. FIG. 3A depicts a construction identical to the one already shown and described except that the compression means takes the form of a multiplicity of helical compression springs 33' arranged in a uniform pattern in recess 34 beneath platen plate 32. The springs are shown in an arrangement of spaced rows, it being understood that each row includes a plurality of such springs.

While in the foregoing I have disclosed embodiments of the invention in considerable detail for purposes of illustration, it will be understood by those skilled in the art that many of these details may be varied without departing from the spirit and scope of the invention.

I claim:

1. A peristaltic pump having a series of bearing assemblies each with concentric inner and outer bearing members freely rotatable with respect to each other;

said inner members being eccentrically mounted upon a drive shaft with the centers of said inner members being equidistant from the axis of said drive shaft and spaced at uniform angular distances thereabout to describe a helix about said axis; means for rotatably supporting said shaft; power means for rotating said shaft; a straight, elongated, resilient tube extending along a line parallel with said shaft and sequentially compressed by each of said outer bearing members of said series for pumping fluid through said tube; and platen means for supporting said tube for sequential compression by said bearing assemblies; said platen means including a rigid floating plate, a support frame fixed in relation to said axis when said pump is in operation, and compression means interposed between said frame and said plate for supporting said plate to maintain said tube in position for sequential compression by said bearing assemblies; said compression means having a resistance to compression generally exceeding the force exerted by said bearing members when sequentially compressing said tube to advance fluid therethrough but being compressible to permit movement of said floating plate away from said axis to relieve compression of said tube and permit backflow therethrough when the pressure of fluid within said tube has exceeded a predetermined maximum level.

2. The pump of claim 1 in which said floating plate has a support surface defining an elongated trough of arcuate transverse section facing said tube; said tube being retained within the concavity of said support surface.

3. The pump of claim 2 in which said support surface has a transverse radius of curvature slightly greater than the outside radius of curvature of each of said bearing assemblies.

4. The pump of claim 3 in which said support surface has a radius of curvature approximating the sum of the outside radius of each bearing assembly, plus the eccentricity of that assembly, plus two times the wall thickness of said resilient tube.

5. The pump of claim 2 in which said support surface has a curvature concentric with said drive shaft.

6. The pump of claim 2 in which said floating plate includes a resilient facing on said support surface.

7. The pump of claim 6 in which said facing is formed of an elastomeric material having a durometer of about 60 to 80.

8. The pump of claim 1 in which said frame defines a recess for receiving said compression means and a portion of said floating plate adjacent said compression means; said floating plate and recess being respectively dimensioned for movement of said plate in directions towards and away from said compression means and for limited movement in directions generally parallel with said axis.

9. The pump of claims 1 or 8 in which said compression means comprises a compressible elastomeric pad.

10. The pump of claim 9 in which said pad is formed of a foam rubber with low hysteresis.

11. The pump of claim 9 in which said recess is elongated in a direction parallel with said axis of said drive shaft; said compression means comprising an elongated compressible elastomeric foam pad having a predetermined resistance to compression and having a width in an uncompressed state substantially less than the width of said recess.

12. The pump of claims 1 or 8 in which said compression means comprises a plurality of compression springs.

13. The pump of claim 8 in which said recess is elongated in a direction parallel with the axis of said drive shaft; said pump including clamping means adjacent opposite ends of said recess for holding said tube in position between said bearing assemblies and said floating plate.

14. The pump of claim 1 in which an elastomeric membrane is supported between said series of bearing assemblies and said resilient tube.

15. A peristaltic pump having a series of bearing assemblies each with concentric inner and outer bearing members freely rotatable with respect to each other; said inner members being eccentrically mounted upon a drive shaft wth the centers of said inner members being equidistant from the axis of said drive shaft and spaced at uniform angular distances thereabout to describe a helix about said axis; means for rotatably supporting said shaft; power means for rotating said shaft; a straight, elongated, resilient tube extending along a line parallel with said shaft and sequentially compressed by each of said outer bearing members of said series for pumping fluid through said tube; platen means for supporting said tube for sequential compression by said bearing assemblies; said platen means including an elongated rigid plate extending in a direction parallel with said axis; and a support frame for supporting said plate in operative relation with respect to said tube; said plate having a support surface defining an elongated trough of arcuate transverse section facing said tube; said tube extending along and being retained within the concavity of said support surface.

16. The pump of claim 15 in which said support surface has a transverse radius of curvature greater than the outer radius curvature of each of said bearing assemblies.

17. The pump of claim 16 in which said support surface has a radius of curvature approximating the sum of the outside radius of each bearing assembly, plus the eccentricity of that assembly, plus two times the wall thickness of said resilient tube.

18. The pump of claim 15 in which said support surface has a curvature concentric with said drive shaft.

19. The pump of claim 15 in which said plate has a resilient facing on said support surface.

20. The pump of claim 15 in which said plate is supported by said frame for movement towards and away from said axis; and compression means disposed between said plate and said frame for supporting said plate and said tube; said compression means being comprssible to permit movement of said plate away from said axis to relieve compression of said tube and permit backflow therethrough when the pressure of fluid within said tube exceeds a predetermined maximum level.

21. The pump of claim 20 in which said compression means comprises an elastomeric pad.

22. The pump of claim 20 in which said compression means comprises a plurality of compression springs.

* * * * *